US00PP23792P2

(12) United States Plant Patent
Hartman

(10) Patent No.: US PP23,792 P2
(45) Date of Patent: Jul. 30, 2013

(54) ***CALADIUM* PLANT NAMED 'PINK SPLASH'**

(50) Latin Name: *Caladium×hortulanum*
Varietal Denomination: Pink Splash

(76) Inventor: Robert Dale Hartman, Lake Placid, FL (US)

( * ) Notice: Subject to any disclaimer, the term of this patent is extended or adjusted under 35 U.S.C. 154(b) by 4 days.

(21) Appl. No.: 13/374,457

(22) Filed: Dec. 29, 2011

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Kent L Bell
(74) *Attorney, Agent, or Firm* — C. A. Whealy

(57) ABSTRACT

A new and distinct cultivar of *Caladium* plant named 'Pink Splash', characterized by its upright plant habit; intermediate plant size; uniform plant habit; vigorous and dense growth habit; relatively short crop time; fancy-type leaves with dark green-colored venation, red purple-colored interveinal areas and dark green-colored margins; and good landscape performance.

4 Drawing Sheets

Botanical designation: *Caladium×hortulanum.*
Cultivar denomination: 'PINK SPLASH'.

BACKGROUND OF THE INVENTION

The present invention relates to a new and distinct cultivar of *Caladium* plant, botanically known as *Caladium×hortulanum*, commercially referred to as a fancy leaf-type *Caladium* and hereinafter referred to by the name 'Pink Splash'.

The objective of the Inventor's breeding program is to create new *Caladium* plants that have uniform plant habit, exceptional container and garden performance and attractive foliage coloration.

The new *Caladium* plant is a naturally-occurring whole plant mutation of *Caladium×hortulanum* 'Elise', not patented. The new *Caladium* plant was discovered and selected by the Inventor as a single plant within a population of plants of 'Elise' in a controlled outdoor nursery environment in Zolfo Springs, Fla. in June, 2008.

Asexual reproduction of the new *Caladium* plant by 'chipping' the tubers (cutting the tuber into segments each segment containing an axillary bud and tuber cortical tissue) in a controlled outdoor nursery environment in Zolfo Springs, Fla. since Apr. 15, 2004 has shown that the unique features of this new *Caladium* plant are stable and reproduced true to type in successive generations of asexual reproduction.

SUMMARY OF THE INVENTION

Plants of the new *Caladium* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Pink Splash'. These characteristics in combination distinguish 'Pink Splash' as a new and distinct *Caladium* plant:

1. Upright plant habit; intermediate plant size.
2. Uniform plant habit.
3. Vigorous and dense growth habit.

4. Relatively short crop time.
5. Fancy-type leaves with dark green-colored venation, red purple-colored interveinal areas and dark green-colored margins.
5. Good landscape performance.

Plants of the new *Caladium* differ primarily from plants of the parent, 'Elise', in leaf coloration as leaves of plants of 'Elise' have green-colored venation, deep pink and green-colored interveinal blotches and green-colored borders.

Plants of the new *Caladium* can also be compared to plants of *Caladium* 'Roselight', not patented. In side-by-side comparisons conducted in Avon Park, Fla., plants of the new *Caladium* differed primarily from plants of 'Roselight' in the following characteristics:

1. Plants of the new *Caladium* were shorter than plants of 'Roselight'.
2. Plants of the new *Caladium* grew faster than plants of 'Roselight'.
3. Leaves of plants of the new *Caladium* were more undulate than leaves of plants of 'Roselight'.
4. Plants of the new *Caladium* and 'Roselight' differed in leaf coloration as leaves of plants of 'Roselight' had rose pink spots and blotches surrounded with green-colored borders.

Plants of the new *Caladium* can be compared to plants of *Caladium* 'Carolyn Whorton', not patented. In side-by-side comparisons conducted in Avon Park, Fla., plants of the new *Caladium* differed primarily from plants of 'Carolyn Whorton' in the following characteristics:

1. Plants of the new *Caladium* grew faster than plants of 'Carolyn Whorton'.
2. Leaves of plants of the new *Caladium* were more undulate than leaves of plants of 'Carolyn Whorton'.
3. Plants of the new *Caladium* and 'Carolyn Whorton' differed in leaf coloration as leaves of plants of 'Carolyn Whorton' had deep rose red-colored venation with pink-colored blotches and green-colored borders.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Pink Splash' grown in a 15-cm container in a shadehouse.

The photograph at the top of the second sheet is a side perspective view of potted plants of 'Pink Splash' grown in 15-cm containers, the plant on the left has had its tuber de-eyed and the plant on the right has not had its tuber de-eyed prior to planting.

The photograph at the bottom of the second sheet is a top perspective view of typical plants of 'Pink Splash' grown in an outdoor nursery.

The photograph on the third sheet is a close-up view of typical freshly-harvested tubers and roots of 'Pink Splash'.

The photograph at the top of the fourth sheet is a comparison view of typical potted plants of the 'Pink Splash' (left) and the parent, 'Elise' (right).

The photograph at the bottom of the fourth sheet is a comparison view of typical potted plants of 'Roselight' (left), 'Pink Splash' (center) and 'Carolyn Whorton' (right).

DETAILED BOTANICAL DESCRIPTION

The aforementioned photographs and following observations and measurements describe plants grown during the spring in 15-cm containers in Avon Park, Fla. in a polypropylene-covered shadehouse (30% shade) and plants grown during the autumn in ground beds in an outdoor nursery in Zolfo Springs, Fla. All plants were grown under environmental conditions and cultural practices which approximate those generally used in commercial shadehouse and outdoor nursery *Caladium* production. During the production of the plants, day temperatures ranged from about 28° C. to 33° C. (shadehouse) or 29° C. to 35° C. (outdoor nursery), night temperatures ranged from about 22° C. to 25° C. (shadehouse) or 23° C. to 26° C. (outdoor nursery) and light levels were about 8,000 foot-candles (shadehouse) or 10,000 to 12,000 foot-candles (outdoor nursery). Plants grown in the shadehouse were six weeks old when the photographs and the detailed description were taken. Plants grown in the outdoor nursery were seven months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Pink Splash'.

Parentage: Naturally-occurring whole plant mutation of *Caladium×hortulanum* 'Elise', not patented.

Propagation:

*Type*.—By "chipping" the tubers.

*Time to initiate roots, summer*.—About seven to ten days at 32° C.

*Time to initiate roots, winter*.—About two to three weeks at 24° C.

*Tuber description* (*outdoor nursery-grown plants*).—Appearance: Multi-segmented; individual segments ovate to round in shape. Height: About 3.3 cm. Diameter: About 4.6 cm. Texture: Thick and starchy; somewhat brittle. Color: Epidermis, freshly harvested, close to 200A and 199A to 199B; epidermis, dried tuber, close to 200A; interior, close to 3C to 3D; axillary buds, close to 155C to 155D. Root description: Thick, fleshy contractile roots; color, close to 155D. Rooting habit: Few lateral branches; moderately dense.

Plant description:

*Plant type*.—Herbaceous perennial; suitable as a potted plant in containers 15-cm to 25-cm and suitable as a landscape plant in shaded areas.

*Plant and growth habit*.—Upright habit; intermediate plant size; inverted triangle; vigorous and dense growth habit; rapid growth rate; petioles and leaves arise from one or more growing points on tubers; petioles mostly upright and slightly leaning outwardly with development.

*Plant height, from soil level to top of foliar plane, shadehouse-grown potted plants*.—About 32 cm to 38 cm.

*Plant diameter or spread, shadehouse-grown potted plants*.—About 45 cm to 48 cm.

*Number of clumps per plant, shadehouse-grown potted plants*.—About five from de-eyed tubers.

*Cataphylls, shadehouse-grown potted plants*.—Length: About 2.7 cm to 3.3 cm. Width: About 8 mm to 12 mm. Shape: Ovate. Apex: Cuspidate. Base: Sheathing the stem. Color, outer surface: Close to N170D finely streaked and tessellated with close to 200B tinged with close to 147A; with development, color becoming closer to N199C stained with close to 187B. Color, inner surface: Close to N155C; colors and patterns visible from outer surface.

Foliage description:

*Length, shadehouse-grown potted plants*.—About 16.4 cm to 20.6 cm.

*Width, shadehouse-grown potted plants* (*flattened*).—About 10.7 cm to 14.2 cm.

*Shape*.—Ovate.

*Apex*.—Cuspidate.

*Base*.—Sagittate, peltate.

*Margin*.—Entire; undulate with broad undulations.

*Texture, upper surface*.—Rugose, glabrous.

*Texture, lower surface*.—Rugose, glabrous; glaucous.

*Venation pattern*.—Pinnate.

*Color, shadehouse-grown potted plants*.—Developing leaves, upper surface: Basal notch: Close to 187A. Area from basal notch to petiole attachment: Close to 185B. Midrib: Darker than 147A. Primary and secondary venation: Darker than 147A. Interveinal areas: Darker than 147A; random spots, close to 63C, 59D and 186C. Borders: Darker than 147A. Developing leaves, lower surface: Basal notch: Close to 187B. Area from basal notch to petiole attachment: Close to 185B to 185C. Midrib: Close to 191A to 191B; proximally, faintly tinged with close to 182C. Primary and secondary venation: Close to 147C. Interveinal areas: Close to 191A to 191B; random spots, close to 64D, 59D and 186C to 186D. Borders: Close to 191A to 191B. Fully expanded leaves, upper surface: Basal notch: Close to 185B to 185C. Midrib: Close to 147A. Primary and secondary venation: Close to 147A and 147A to 147B. Interveinal areas: Close to 63C, 63D and 64D. Borders: Close to 147A tinged with close to N189A. Fully expanded leaves, lower surface: Basal notch: Close to 185B. Area from basal notch to petiole attachment: Close to 185C. Midrib: Close to 191B, 194B and 147B. Primary venation: Close to 147B, 191A and 195C. Areas surrounding primary venation: Close to 155A. Secondary venation: Close to 191A. Interveinal areas: Random sectors, close to 55A, 62C, 62D and 63C. Borders: Close to 191A.

*Petiole*.—Aspect: Mostly erect and slightly outwardly leaning with development; flexible. Length, shadehouse-grown potted plants: About 23 cm to 32.7 cm. Diameter, distal, shadehouse-grown potted plants: About 4 mm. Diameter, proximal, shadehouse-grown potted plants: About 5 mm to 8 mm. Color, shadehouse-grown potted plants: Close to N170D tinged with close to 147A to 147C and streaked, stippled and speckled with close to 200A tinged with close to 147A. Wing length, shadehouse-grown potted plants: About 5 cm to 6 cm. Wing diameter, shadehouse-grown potted plants: About 5 mm to 8 mm. Wing color, shadehouse-grown potted plants, outer surface: Close to N170D finely streaked and tessellated with close to 200B tinged with close to 147A; towards the apex, often tinged with close to 187D. Wing color, shadehouse-grown potted plants, inner surface: Close to N155C; colors and patterns visible from outer surface.

Inflorescence description: Inflorescence initiation and development have not been observed on plants of the new *Caladium*.

Disease & pest tolerance/resistance: Plants of the new *Caladium* have been observed to have above average tolerance to *Xanthomonas* Leaf Spot and average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and suitable for USDA Hardiness Zones 8A to 11.

It is claimed:

1. A new and distinct *Caladium* plant named 'Pink Splash' as illustrated and described.

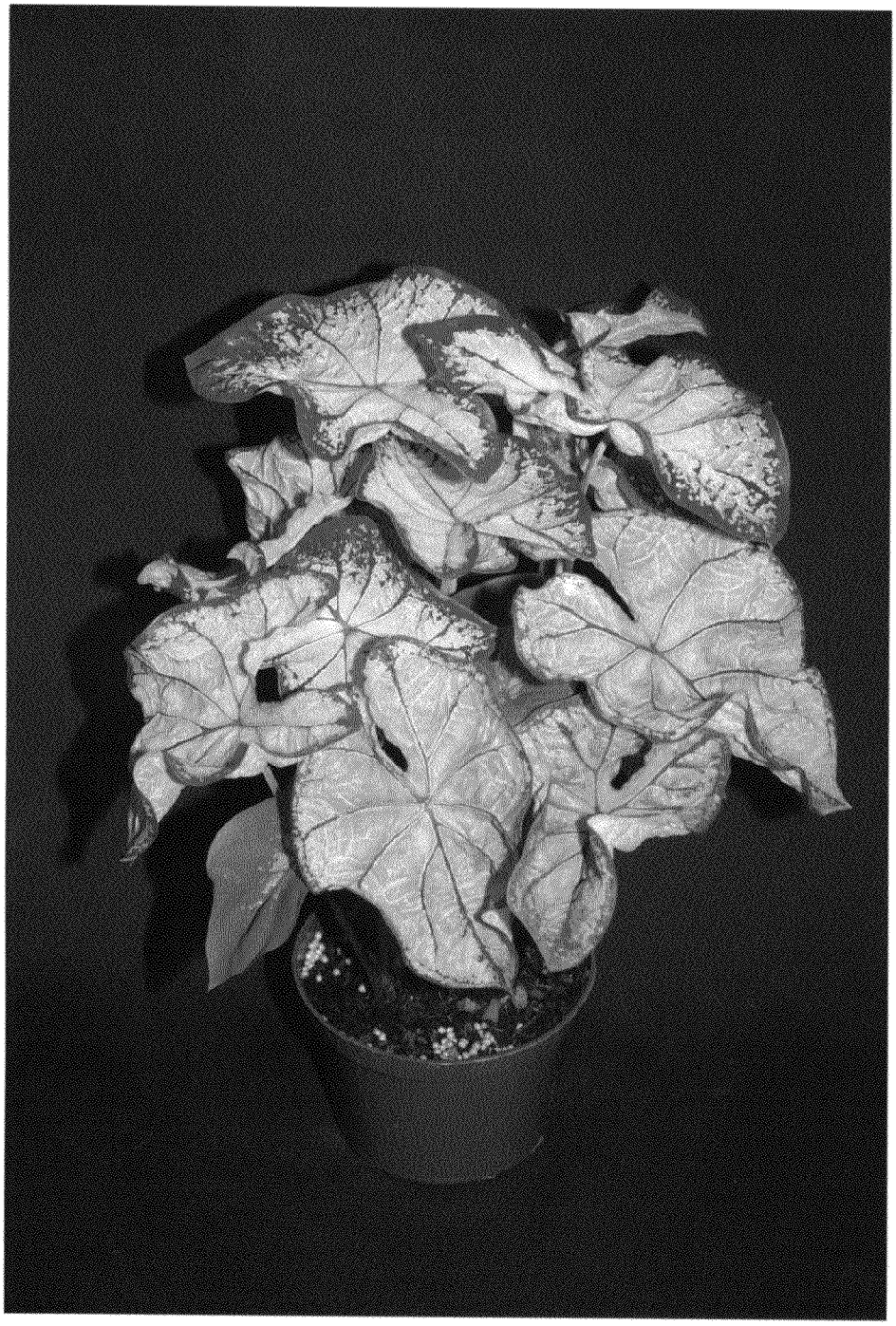

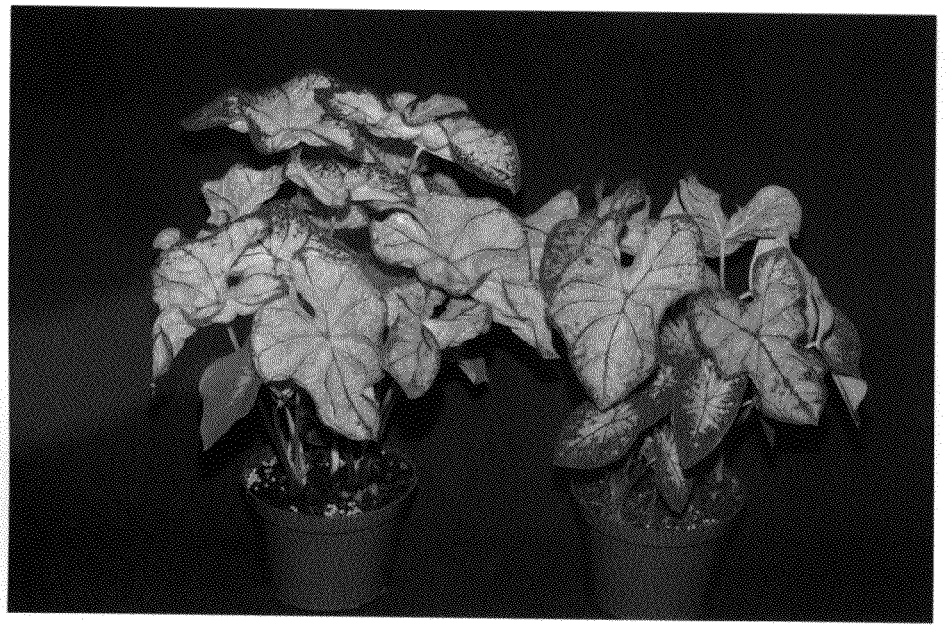
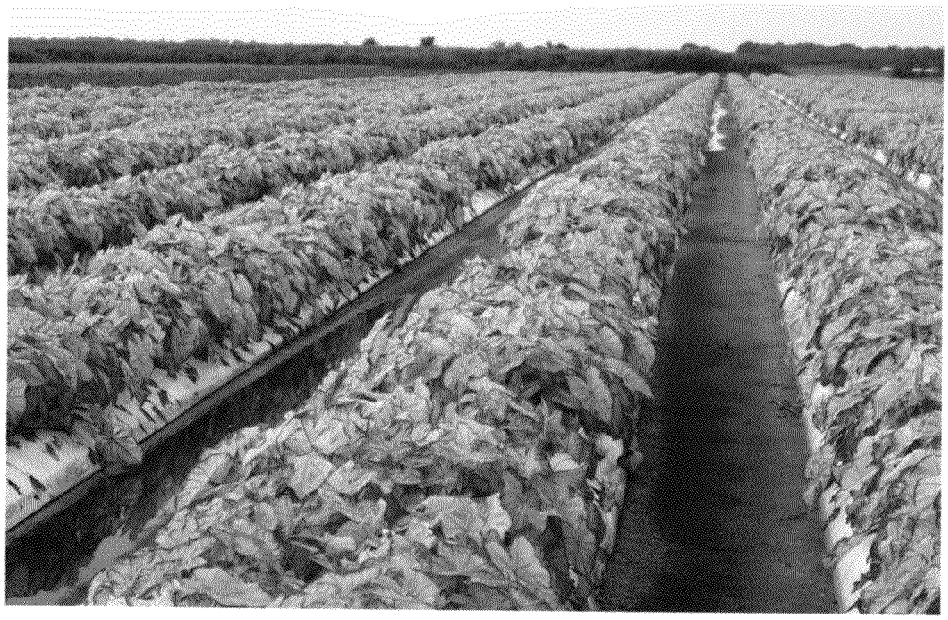

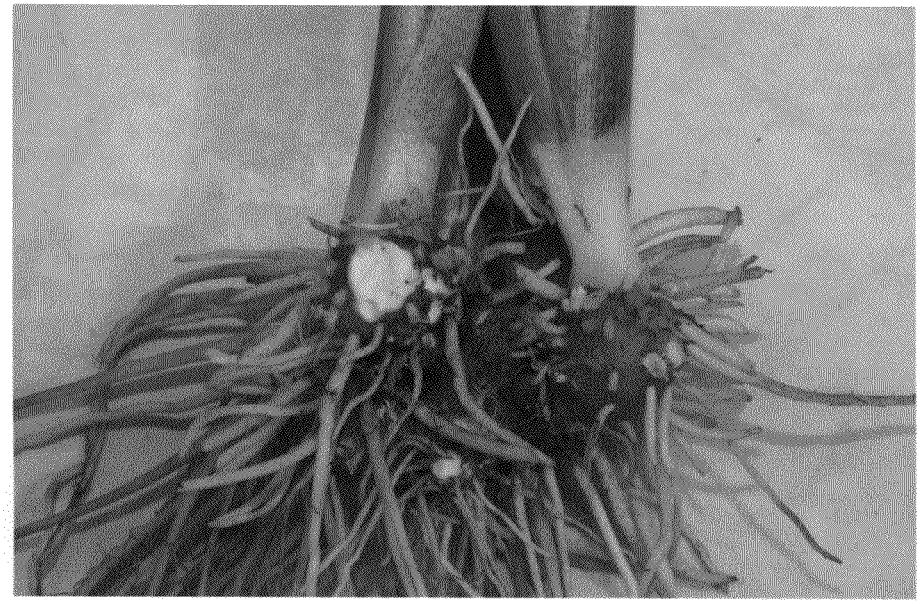

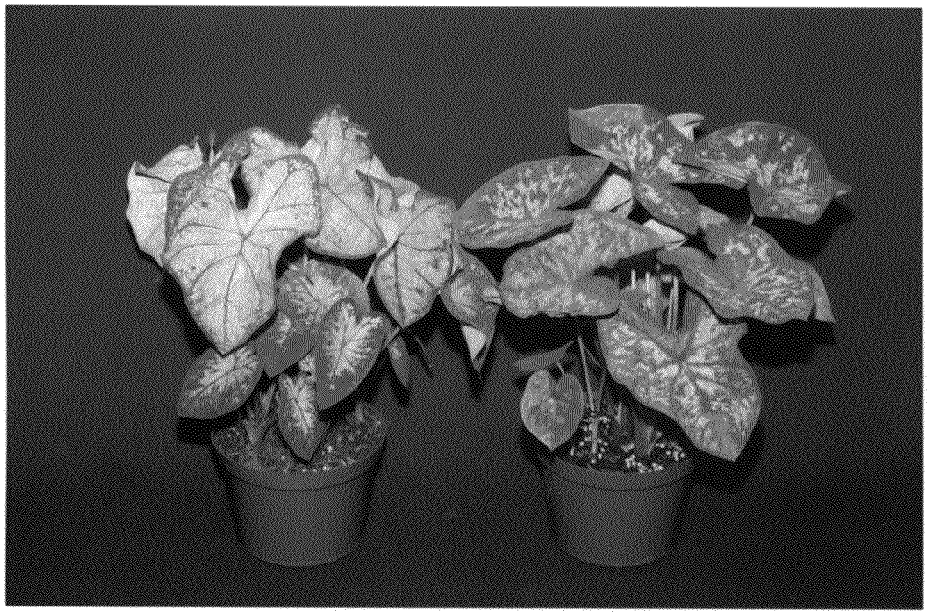
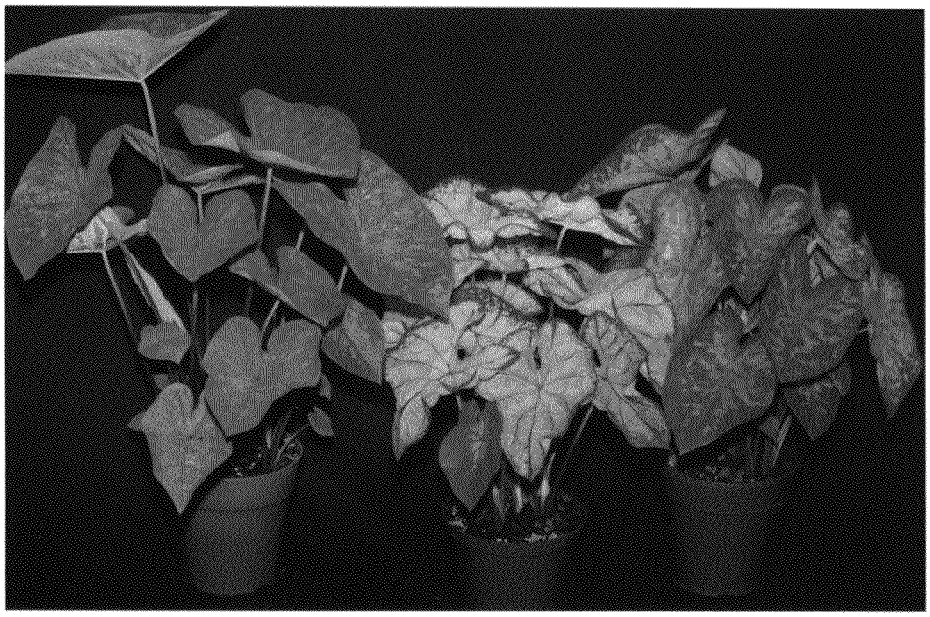

* * * * *